United States Patent [19]
Yoon

[11] Patent Number: 5,217,030
[45] Date of Patent: Jun. 8, 1993

[54] MULTI-FUNCTIONAL INSTRUMENTS AND STRETCHABLE LIGATING AND OCCLUDING DEVICES

[76] Inventor: InBae Yoon, 2101 Highland Ridge Dr., Phoenix, Md. 21131

[21] Appl. No.: 720,382

[22] Filed: Jun. 25, 1991

Related U.S. Application Data

[62] Division of Ser. No. 446,555, Dec. 5, 1989, Pat. No. 5,026,379.

[51] Int. Cl.$^5$ ............................................. A61B 17/00
[52] U.S. Cl. ............................ 128/898; 606/151; 606/140
[58] Field of Search ............... 606/140, 141, 151, 206, 606/157; 128/898

[56] References Cited

U.S. PATENT DOCUMENTS

| | | |
|---|---|---|
| 3,967,625 | 7/1976 | Yoon .................................. 606/141 |
| 4,085,743 | 4/1978 | Yoon .................................. 606/140 |
| 4,103,680 | 8/1978 | Yoon .................................. 606/140 |
| 4,249,533 | 2/1981 | Komiya . |
| 4,374,523 | 2/1983 | Yoon .................................. 606/141 |
| 4,471,766 | 9/1984 | Terayama . |
| 4,493,319 | 1/1985 | Polk et al. . |
| 4,788,966 | 12/1988 | Yoon . |
| 4,869,268 | 9/1989 | Yoon .................................. 606/151 |

Primary Examiner—Stephen C. Pellegrino
Assistant Examiner—Gary Jackson

[57] ABSTRACT

Methods of ligating, severing and plugging an anatomical tubular structure utilizing an applicator for placing a flexible, resilient ligature or plug in engagement with the anatomical tubular structure. In a method of ligating and severing an anatomical tubular structure, a ligature is applied with the use of forceps movable within a tubular member of the applicator carrying at least one ligature, the forceps is removed from the tubular member, a cutting instrument is inserted through the tubular member and the anatomical tubular structure is cut adjacent the ligature. In a method of ligating an anatomical tubular structure, the anatomical tubular structure is anesthetized with an instrument passing through the tubular member of the applicator prior to placing the ligature in engagement with the anatomical tubular structure. In a method of plugging an anatomical tubular structure, a resilient plug is mounted on an elongate member of the applicator, the distal end of the elongate member is positioned adjacent the anatomical tubular structure using an endoscope and the plug is positioned within the anatomical tubular structure.

6 Claims, 8 Drawing Sheets

MULTI-FUNCTIONAL INSTRUMENTS AND STRETCHABLE LIGATING AND OCCLUDING DEVICES

This is a divisional application of application Ser. No. 07/446,555, filed Dec. 5, 1989 now U.S. Pat. No. 5,026,379.

This invention relates generally to surgical devices and instruments, and, more particularly, to a multi-functional endoscopic and/or non-endoscopic surgical device, which may be used to accomplish all phases of applying an occluding ligature to an anatomical tubular or non-anatomical tubular organ structure. For example, the invention may be used to occlude or sever the Fallopian tubes of a female or the vas deferens of a male, or for vascular ligation, plugging anatomical lumen or encapsulating organ tissue structure.

Currently, there are numerous practices employed to effect sterilization in women and men. One practice is to cut and tie the Fallopian tubes. Another practice is the use of an endoscope through which the Fallopian tubes can be electrically coagulated by a bipolar or unipolar instrument to produce permanent sterilization. Another practice is the use of a deformable clip or elastic ring for clipping or occluding the tubes, vas deferens, blood vessels or other organ structures. Clipping and occluding procedures are potentially reversible disconnections of anatomical tubular structures by application of one or more clips to the tubular structures or one or more elastic rings to loops formed in the tubular structures. Means and methods for accomplishing this procedure with elastic rings are fully disclosed in my previous U.S. Pat. Nos. 3,870,048, 3,911,923, 3,989,049, the teachings of which are incorporated herein by reference, and others. The electric unipolar or bipolar technique involves electrical cauterization of the Fallopian tubes, vas deferens or blood vessels. Each of these procedures has its own, well known attendant advantages and disadvantages. The electric technique has less chance of reversibility than clipping or occluding by elastic ring by way of reconstructive surgery.

Prior to the instant invention, there was no multipurpose instrument or device which could be used to accomplish any one of the tubular structure occluding techniques noted above, and the attendant procedures of injecting anesthesia, insufflation of an inert gas such as carbon dioxide into the surgical field, taking a biopsy, coagulation, utilizing suction, etc.

In summary, the electric coagulation technique, clip technique and ring technique have their own advantages and disadvantages which are also related to the individual patient's age and the condition of the tubular structure. In order to utilize the advantages of the above-mentioned three major types of laparoscopic (endoscopic) anatomic tubular occlusion techniques and eliminate the disadvantages of these techniques, the instrument of the present invention can apply selectively all three techniques depending on the individual circumstances at the time of the surgical procedure, and also can effect reversible sterilization without reconstructive surgery (in other words, by simple removal of the occluding devices, patients can be restored to their fertility stages). There are two reversible occlusion techniques in addition to the above-mentioned techniques which are plugging and Fimbrial encapsulation, both of which can be accomplished with the instrument of the present invention. This new and improved instrument used with various occluding devices offers not only permanent or reversible occlusion but also various other endoscopic surgical procedures including ligating, clipping, plugging and/or encapsulating surgical procedures with interchangeable instrumentation.

SUMMARY OF THE INVENTION

Accordingly, it is a principal object of this invention to provide a multi-purpose surgical device for occluding an anatomical tubular structure by any of the presently known techniques, the device being further useful to accomplish all the ancillary procedures to accomplish occlusion of an anatomical tubular structure (e.g., sterilization).

It is a further object of the invention to provide an improved, flexible and resilient or stretchable ligature for an anatomical tubular structure which has sufficient elastic memory to accomplish occlusion once released around or across an anatomical structure, such as the Fallopian tubes or vas deferens.

It is another object of the invention to provide an improved, multi-functional surgical device for occluding an anatomical tubular structure which is further combined with illumination and viewing means (e.g., a laparoscope), the viewing means including a swivel connection to the multi-functional surgical device, thereby rendering the entire structure far easier to use in accomplishing a surgical procedure.

Yet another object of the invention is to provide a surgical device to accomplish sterilization by any one of a wide variety of methods, such as electrical cauterization, cutting and tying the tubes, occlusion of tubes, plugging the utero-tubal junction or Fimbrial encapsulation, by application of a clip, plug, or elastic ring, or application of a shape-retaining, stretchable clip.

Still another object of the invention is to provide a new and improved stretchable clip for occluding an anatomical tubular structure, the clip or ligature having sufficient elastic memory so as to grasp and firmly occlude the anatomical tubular structure after release from an opened, distended state.

A further object of the invention is to provide such an improved, multi-functional surgical instrument having interchangeable forceps permitting numerous surgical procedures with a single instrument system.

BRIEF DESCRIPTION OF THE DRAWINGS

Further and more complete objects and advantages of the invention will become readily apparent by reference to the following drawings in which.

DESCRIPTION OF THE PREFERRED EMBODIMENTS

Figures 3, 4, 5:
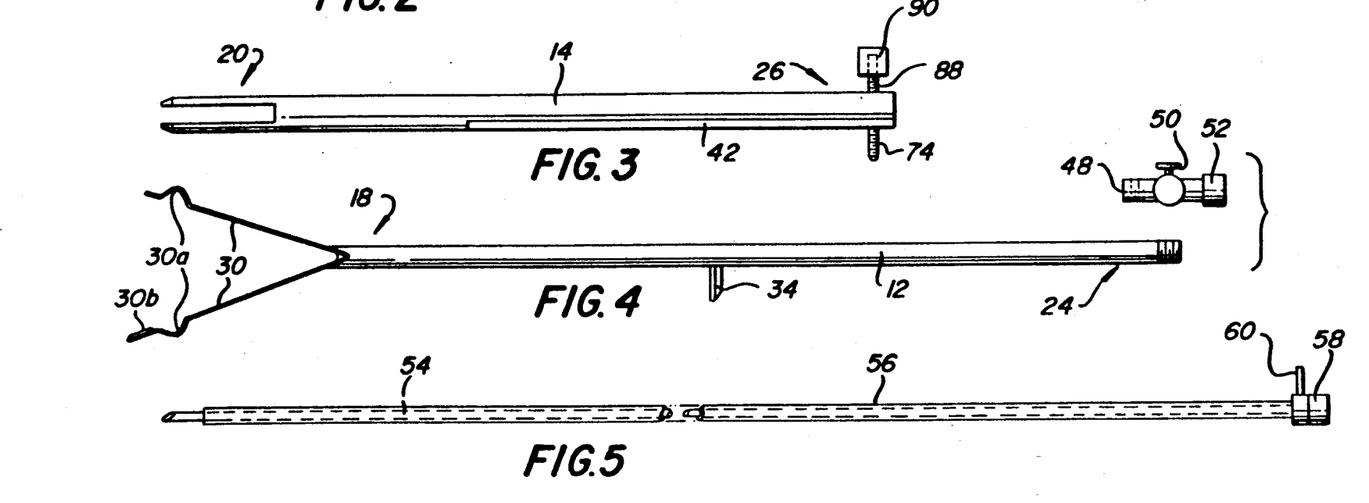
FIG. 3 is a side, elevational view of the middle tube or cylinder of the device shown in FIG. 1, drawn to an enlarged scale.
FIG. 4 is a partially exploded, side, elevational view of the inner member or cylinder of the device shown in FIG. 1, drawn to an enlarged scale.
FIG. 5 is a side, elevational view of an additional, elongate surgical instrument which may be inserted through the inner member illustrated in FIG. 4.

Referring now to the drawings by reference character and, in particular, to FIGS. 1-4 thereof, a preferred embodiment of the surgical device 10 is shown, configured to apply either an elastic ring or stretchable clip onto a tubular, anatomical structure. Surgical device 10 includes an inner tubular member 12 which is slidably, telescopically received within a middle, tubular member 14 which, in turn, is telescopically, slidably received within an outer, tubular member 16. Each tubular member 12, 14 and 16 has a distal end 18, 20 and 22 and a proximal end 24, 26 and 28, respectively. Inner tubular member 12 has a forceps 30 of any desired construction extending from its distal end 18. The inner tubular member 12 may be of unitary construction or may be of two-piece telescoping construction to prevent the proximal end thereof from extending out of the proximal end of the device 10 in certain application. Forceps 30 are extended from and retracted into distal end 20 of middle tubular member 14 by sliding inner tubular member 12 within middle tubular member 14. This is accomplished by moving a surrounding handle 32 which engages a peg 34 which depends from a mesial portion of inner tubular member 12, as is best illustrated in FIG. 4. The term "forceps" in the present application is intended to cover any type of gripping or holding means including suction means or the like, the forceps shown in FIG. 4 having concave portions 30a at the distal ends of the forceps members and a hole 30b in the end of the lower forceps member.

Figures 6, 7, 8A, 8B:
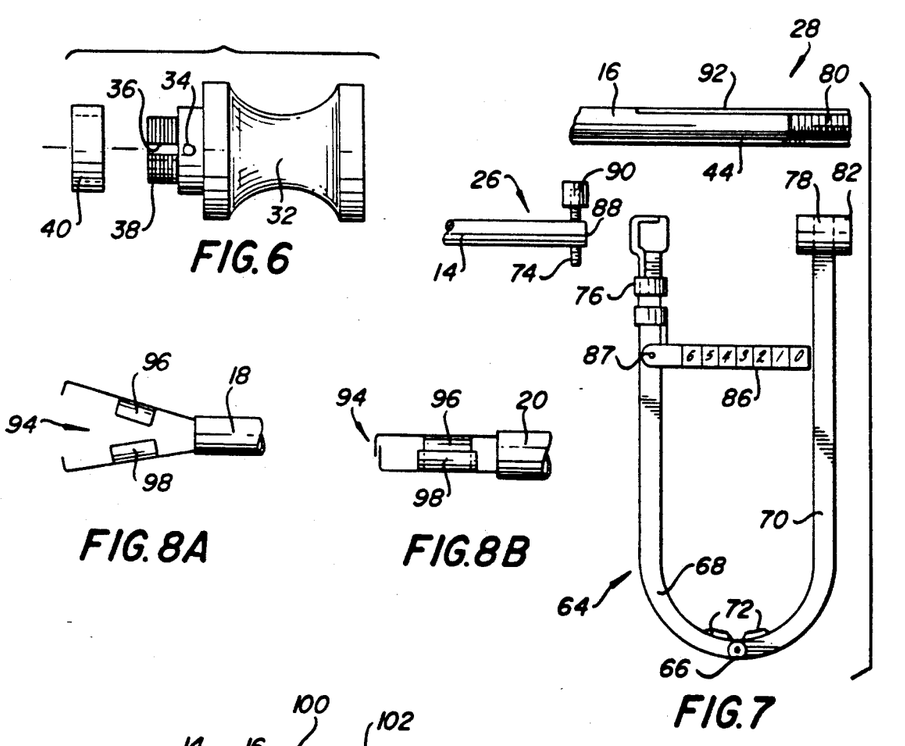
FIG. 6 is an exploded, bottom view of a handle which is used to extend and retract a forceps, the view being taken from the center portion of FIG. 1 and drawn to an enlarged scale.
FIG. 7 is an elevational, exploded view taken from the right hand portion of FIG. 1 and drawn to an enlarged scale.
FIGS. 8A and 8B are partial side, elevational views illustrating a modification of the invention shown in FIG. 1, wherein the forceps at the left of the view are provided with elements for taking a biopsy, FIG. 8A showing the instrument open and FIG. 8B showing the instrument closed.

The structure of handle 32 is best shown in FIG. 6. A slot 36 is formed at the forward end 38 of handle 32, and peg 34 is trapped therein by a cap 40 threaded onto end 38. Referring to FIG. 3, middle tubular member 14 has an elongated slot 42 formed in the bottom thereof and outer tubular member 16 has a similar slot 44 formed in the bottom thereof. Slots 42 and 44 have, generally, the same dimensions and peg 34 extends through slots 42, 44 as can be appreciated from FIG. 1. Thus, movement of handle 32 back and forth effects extension and retraction of forceps 30 from distal end 30 of middle tube 14.

In order to accomplish an electrical cauterization procedure, peg 34 may also be a bipolar or unipolar electrical connector. Inner tubular member 12 may include an additional electrical connector 46 which is shown at the upper right hand portion of FIG. 1. Connector 46 may be a unipolar or bipolar electrical connector.

Figures 1, 2:
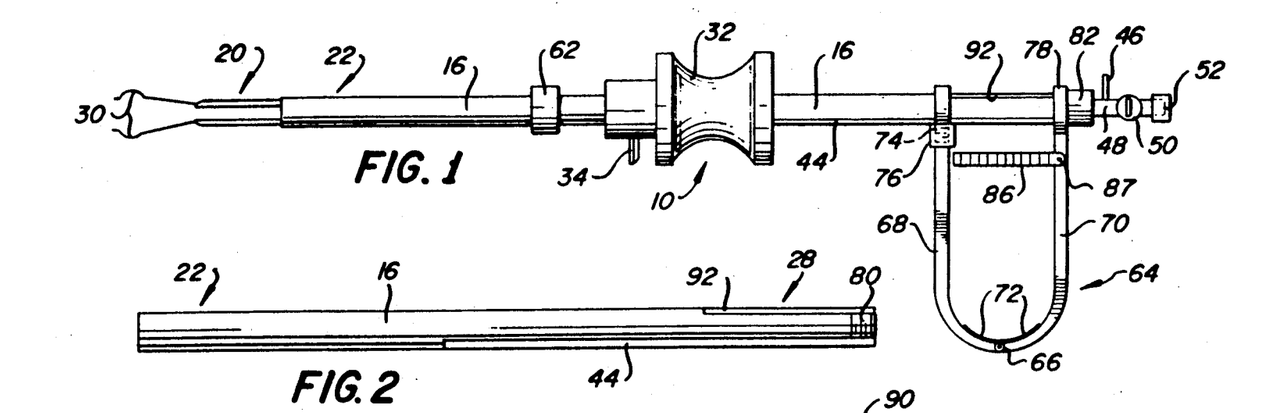
FIG. 1 is a side, elevational view of a preferred embodiment of the surgical device of this invention.
FIG. 2 is a side, elevational view of the outer tube or cylinder of the device shown in FIG. 1, drawn to an enlarged scale.

Proximal end 24 of member 12 may be threaded to receive an additional tubular segment 48 which may be provided with a stop cock 50 and a port 52. Port 52 may be connected, for example, to a pressurized supply of an inert gas such as carbon dioxide (not shown). Obviously, the gas will pass through the tubular member 12 to the surgical field. After the gas is introduced, stop cock 50 is closed to prevent the escape of the gas.

Turning now to FIG. 5, an instrument is illustrated which may be inserted through proximal end 24 of inner tubular member 12, into the surgical field. This instrument may be in the form of an elongated needle or cannula 54, housed within a protective shield 56 forming insulation when the needle conducts electricity or a shield when the needle is used as a laser delivery device or probe. This instrument may be provided to effect electrical cauterization. For example, end 58 of the instrument may be provided with a unipolar electrical connector 60. This instrument might also be used for the injection of anesthesia, application of an inert gas such as carbon dioxide into the surgical field, application of laser energy to the surgical field, or for other, known purposes.

With further reference to FIG. 1, a rotatable, threaded connector member 62 is located on outer tubular member 16 between distal end 22 and the handle 32 for the purpose of releasably securing the device 10 to a laparoscope (not shown) or the like.

Referring now to FIG. 1, right hand portion, and FIG. 7, a handle structure is shown which is employed to eject a stretchable ligature from the distal end 20 of middle tubular member 14. A generally U-shaped handle 64 is provided which may be in one piece or may be centrally bifurcated at 66 into a first handle member 68 and a second handle member 70. Handle members 68 and 70 may be pivotally connected at the bifurcation point 66 and a spring 72 may be provided to urge members 68 and 70 apart.

With reference to FIG. 3, proximal end 26 of middle tubular member 14 includes a depending, threaded post 74. The upper end of handle member 68 is provided with an internally threaded member 76 for securing post 74 to the handle member 68. Of course, post 74 extends downwardly through the elongated slot 44 of outer tubular member 16. The upper end of second handle member 70 includes a capture ring 78 through which proximal end 28 of outer tubular member 16 is inserted. The proximal end 28 of tubular member 16 is externally threaded at 80 to receive an internally threaded capture cap 82. Thus, as handles 68 and 70 are squeezed together, distal end 22 of outer tubular member 16 moves towards and slides over the distal end 20 of middle tubular member 14, thus to eject a stretchable ligature mounted on distal end 20.

Figure 10:
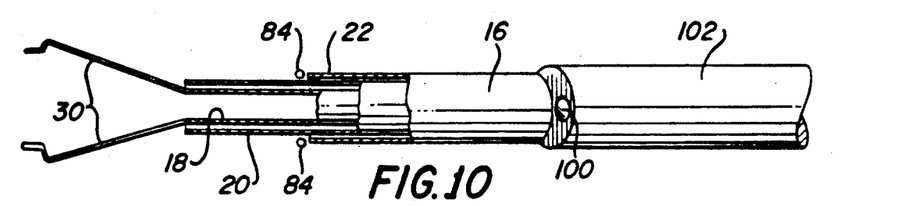
FIG. 10 is a side elevational, enlarged scale, partial sectional view of the forceps or proximal end of the invention.

The methodology for accomplishing this is well disclosed in my prior U.S. Pat. No. 3,989,049. This patent discloses the ejecting of one or more elastic rings, such as is shown at 84 in FIG. 10. If multiple stretchable ligatures, plugs or caps are mounted on distal end 20, a gauge 86 may be provided which controls the movement of the outer tubular member 16 to eject the ligatures one at a time and to indicate the number of ligatures being ejected. The gauge may be mounted on either handle member 68 (FIG. 7) or handle member 70 (FIG. 1). The gauge may be pivotally mounted as is shown at 87 so that it may be swung out of the way if it is not to be used and may be used as a locking or control device for various occluding ligatures or devices.

For further security of structure, proximal end 26 of middle tubular member 14 may be provided with a second, upstanding vertical post 88 having a head 90. Proximal end 28 of outer tubular member 16 would be provided with an upper, elongate slot 92 within which post 88 rides as outer tubular member 16 is moved axially relative to middle tubular member 14, to eject a stretchable ligature in the manner just described.

With reference to FIGS. 8A and 8B, a forceps structure is shown for taking a biopsy. An interchangeable inner tubular member 12 is provided with forceps 94 having cooperating, biopsy box members 96 and 98. Retraction of forceps 94 in the manner described above causes the forceps to close and grasp tissue at the ends while the biopsy box members 96 and 98 cut and enclose a piece of tissue.

Figure 9:
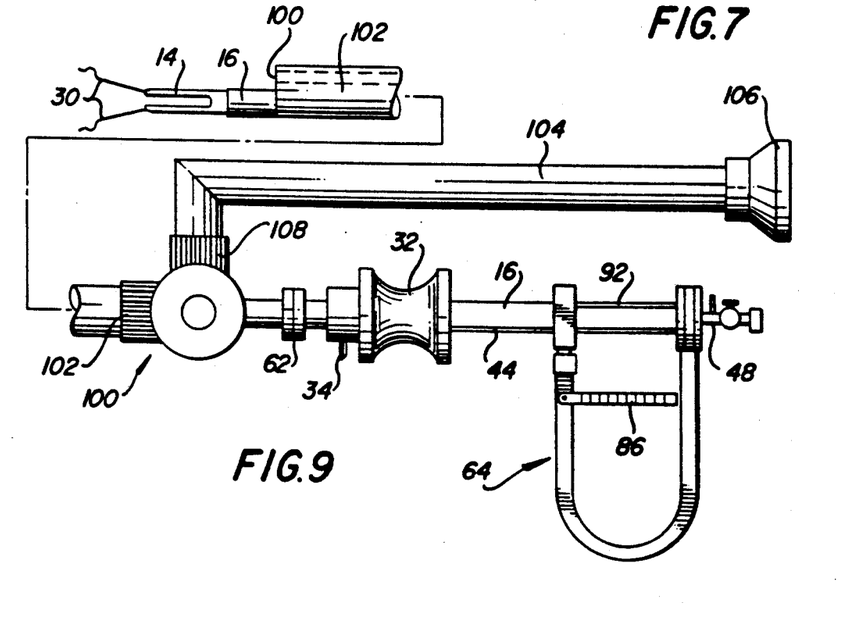
FIG. 9 is a side, elevational view of the device or instrument shown in FIG. 1 provided with a laparoscope, there being a swivel connection of the laparoscope with respect to the instrument.

With reference to FIG. 9, the instrument 10 of FIG. 1 is shown in combination with a laparoscope 100. Outer tubular member 16 is received with main body 102 of laparoscope 100. A light source is provided at 104. Laparoscope 100 includes an offset portion 104 having an eyepiece 106. Conveniently, offset portion 104 is connected to main body 102 by a swivel connection 108. Swivel connection 108 permits the offset portion 104 to be moved to a more comfortable position for the surgeon. More specifically, the surgeon need not stand directly behind the laparoscope but may more comfortably, view the surgical field from the side of the instrument.

Figure 11:
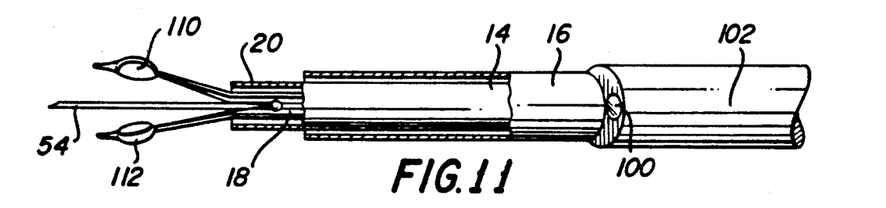
FIG. 11 is a view similar to FIG. 10, but showing other instruments extended from the proximal end of the device.

FIG. 11 illustrates another forceps instrument for taking a biopsy including cooperating cutting members 110 and 112 disposed on opposite sides of instruments 54. The cutting portions 110 and 112 of the forceps members are concave to cut and capture tissue therebetween, and pointed portions extend distally from the cutting portions for use in grasping the tissue prior to cutting for biopsy purposes.

As briefly discussed above and disclosed in extended detail in, for example, my prior U.S. Pat. Nos. 3,911,923 and 3,989,049, one method of applying a stretchable ligature to an anatomical tubular structure includes extending forceps 30 about the tube, withdrawing forceps 30 into proximal end 20 of middle tubular member 14 so as to crimp the tube and form a loop therein (e.g., as shown here in FIGS. 22 and 23) and then moving outer tubular member over middle tubular member 14 to eject a stretchable ligature (such as elastic member 84) onto and over the looped, anatomical tubular structure.

Figure 12:
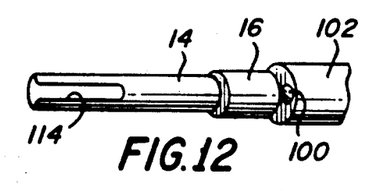
FIG. 12 is a partial elevational view of an embodiment of the invention having a tissue receiving slot formed in the proximal end of the middle tubular member.

When the distal end 20 of middle tubular member 14 is completely closed, difficulty has been found in withdrawing an adequate amount of anatomical tubular structure into the device so as to assure effective occlusion of tissue upon placement of the stretchable ligature therearound. With reference to FIG. 12, a distal end 20 of middle tubular member 14 is illustrated having a tissue receiving slot 114 formed therein. Excess tissue may be located within the slot during the procedure so that an adequate amount of tubular structure is withdrawn into the middle tubular member 14. Also, the slot 114 allows the middle tubular member to expand somewhat to facilitate the entry of the tubular structure therein.

Figure 13:
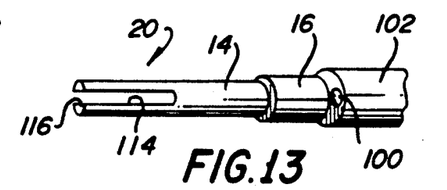
FIG. 13 is a view similar to FIG. 12 but showing a pair of slots formed in the middle member distal end.
Figure 14:
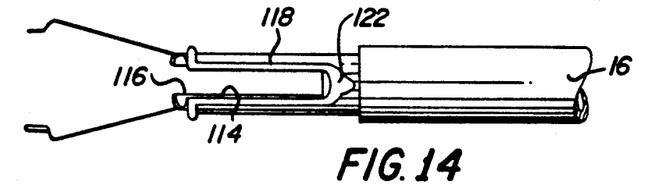
FIG. 14 is a view similar to FIG. 13 but drawn to an enlarged scale and illustrating one embodiment of a stretchable clip of this invention mounted on the distal end of the middle member.
Figure 15A:
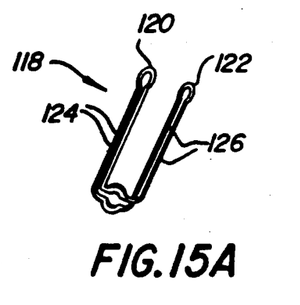
FIG. 15A is a perspective view of the stretchable clip illustrated in FIG. 14.

As shown in FIG. 13, a pair of tissue receiving slots 114, 116 are provided which have generally similar dimensions. This structure permits application of a stretchable ligature laterally across an anatomical tubular structure and thus eliminates the need for forming a loop in the tube being ligated. Depending on the type of ligating device and the distal configuration of the forceps being utilized, the tissue may or may not be moved into the slots of the middle tubular member. For example, where forceps with kissing ends are used with a ligating device as shown in FIG. 15a, the tissue is moved to the distal end of the middle tubular member and the ligature is applied thereto without entry of the tissue into the slots. When forceps with overlapping ends are used with a stretchable ring device, the tissue may be moved into the slots before the ring is applied thereto. The slots 114 and 116 also provide increased space to accommodate tissue to be engaged, such as tubes to be ligated which have a size so as not to be easily received in middle member 14 when forceps 30 draw the tube into the middle member to form a loop in the tube. That is, in a manner similar to that described above with respect to the single slot embodiment of FIG. 12, slots 114 and 116 accommodate excess tissue to permit positioning of the tissue at the distal end of member 14 and also allow the distal end of the middle member to expand to accommodate a greater tissue volume. To this end, opposed slots 114 and 116 are disposed between the opposed members of forceps 30, as shown in FIG. 14; and, preferably, a plane passing centrally through slots 114 and 116 is substantially transverse to a plane passing centrally through the opposed forceps members. Accordingly, the slots are disposed in the distal end of the middle member at positions not angularly aligned with the forceps members; and, preferably, the slots 114 and 116 are aligned with the plane of the loop of a tube to be ligated such that the slots provide maximum accommodation for excess tube tissue.

Figure 15B:
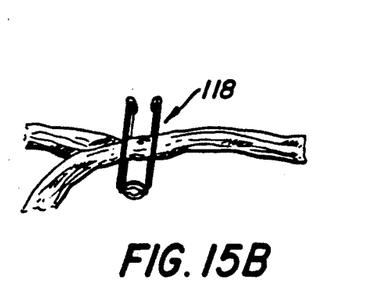
FIG. 15B is an elevational view showing the clip illustrated in FIG. 15A occluding a tubular anatomical structure such as a Fallopian tube.

A first embodiment of a stretchable ligature of this invention is illustrated in FIG. 15A. This ligature includes a one-piece clip 118, formed of any non-tissue reactive, medical grade material that is suitable for implantation in the human body, having base portions 120, 122 and pairs of cooperating legs 124, 126. At least the base portions 120, 122 are made of a material having a sufficient elastic memory to force the pairs of legs 124, 126, with or without engaging teeth, closed after placement of the clip 118 over an anatomical tubular structure. Clip 118 is opened and forced over distal end 20 of middle tubular member 14 in a manner to be described below. This is shown in FIG. 14. Forceps 30 are then manipulated to grasp an anatomical tube and pull the same within the slots 114, 116. Outer tubular member 16 is then pushed over tubular member 14 to eject both clip 118 and the anatomical tubular tissue from the instrument. When ejected, the legs 124, 126 grasp and occlude the anatomical tubular structure under the urging of the base 120, 122. The result is illustrated in FIG. 15B.

Figure 16:
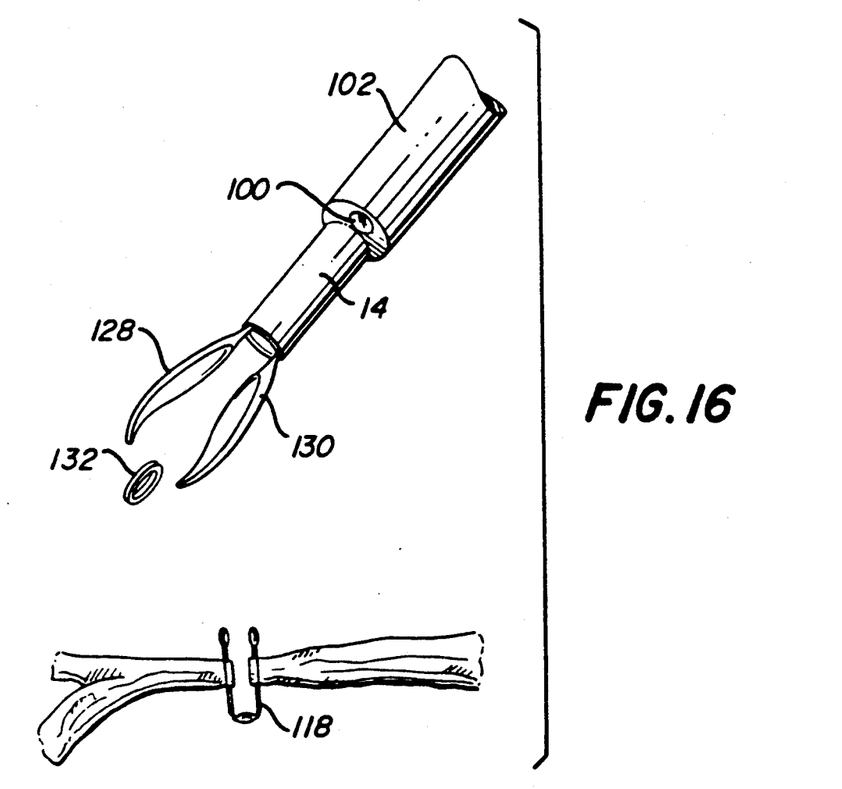
FIG. 16 is an elevational, exploded view illustrating placement of the clip shown in FIG. 15A and the further step of surgical removal of a segment of the anatomical tubular structure located between the legs of the clip by a biopsy forceps.

When conducting a sterilization procedure and in order to assure a permanent sterilization, the section of tubular tissue between the legs 124, 126 may be severed and removed. This is illustrated in FIG. 16. After placement of clip 118 as described above, inner tubular member 12 may be replaced with another instrument having spring-loaded blades 128, 130 at the proximal end 18 of the member 12 similar to the structure shown in FIG. 11. The blades are brought together by retracting the member 12 within the intermediate tubular member 14, thus to sever a section 132 from the anatomical tubular structure, it being appreciated that the concave portions serve to cut and capture the tissue 132 while the pointed distally extending portions service to hold the tissue. Thereafter, an instrument 54 (FIG. 5) can be inserted within the inner tubular member 12, the instrument 54 being connected to a source of suction (not shown). Instrument 54 is then extended into the surgical field and suction is applied to remove the excised piece 132.

Figure 17:
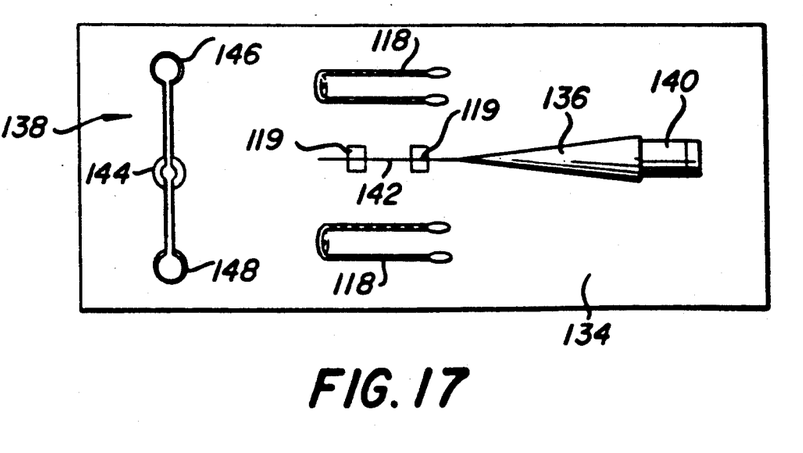
FIG. 17 is a plan view of a package of clips and rings and the parts of a loading device for mounting the clips onto the instrument.

FIG. 17 illustrates a package 134 including a pair of clips 118, a pair of elastic rings 119, a loading device 136 and a pushing device 138. In order to load a clip 118 onto distal end 20 of intermediate tubular member 14, end 140 of loading device 136 is inserted into the distal end 20. Clip 118 is slipped onto the narrowed end 142 of loading device 136. Pushing device 138 has a central aperture 144 and spring ends 146, 148. Pushing device 138 is inserted onto loading device 136 with end of 142 of loading device inserted through central aperture 144 of pushing device 138. The clip is then slid up the conical-shaped loading device 136 and pushed onto distal end 20 of intermediate tubular member 14. The result is illustrated in FIG. 14. Similar structure for loading an elastic ligature is disclosed in my prior U.S. Pat. Nos. 3,911,923 and 3,989,049.

Figures 18A, 18B:
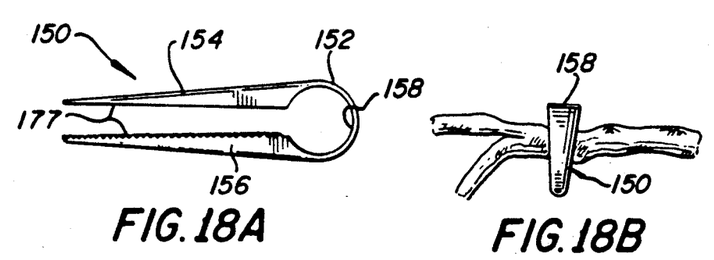
FIG. 18A is a side, elevational view of another stretchable clip of this invention in an open position.
FIG. 18B shows the clip of FIG. 18A in place about an anatomical, tubular structure such as a Fallopian tube.
Figure 19A:
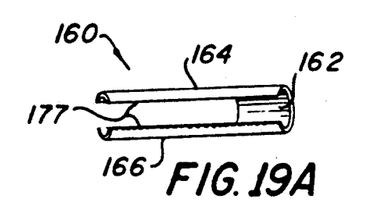
FIGS. 19A and 19B are views similar to FIGS. 18A and 18B, respectively, showing another embodiment of the stretchable clip of this invention.
Figure 19B:
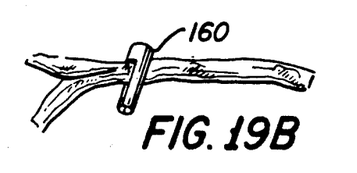
Figure 20A:
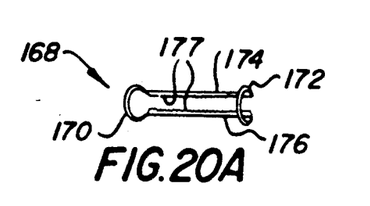
FIGS. 20A and 20B are views similar to FIGS. 18A and 18B, showing yet another embodiment of the stretchable clip of this invention.
Figure 20B:
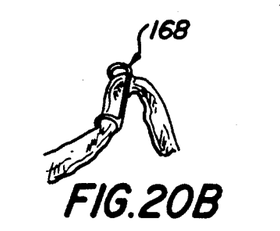

Other embodiments of the ligatures of this invention are illustrated in FIGS. 18-20 inclusive. In FIG. 18A, a clip 150 is shown including an elastic memory base 152 and a clamp portion in the form of a single pair of cooperating legs 154, 156. An opening 158 is formed in base 152 so that the clip 150 may be inserted onto proximal end 20 of intermediate tubular member 14 in the manner just discussed. FIG. 18B illustrates clip 150 after installation.

FIG. 19A shows a clip 160 having an elastic memory base 162 and opposed legs 164, 166. Base 160 may extend the full length of legs 164, 166 (not shown). Clip 160 is illustrated in place, ligating an anatomical tubular structure, in FIG. 19B.

Another clip 168 is illustrated in FIG. 20A, including a pair of elastic memory bases 170, 172 joined by opposed legs 174, 176. FIG. 20B shows the clip 168 ligating an anatomical tubular structure.

If desired, the facing surfaces of the legs of each of the clips just discussed may be serrated as is shown at 177 in order to assure that the clip is securely locked onto the anatomical tubular structure being ligated.

Figures 21, 22:
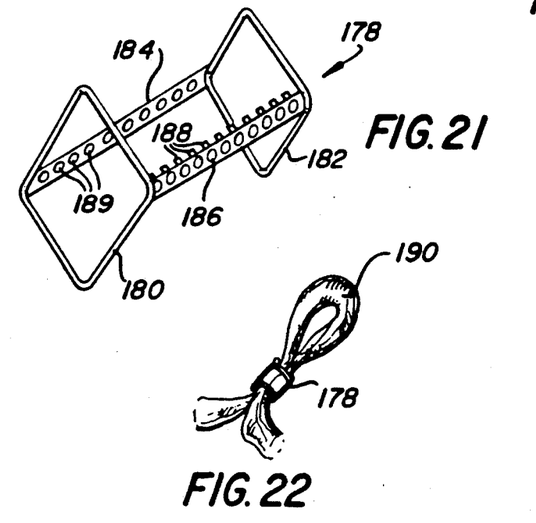
FIG. 21 is a perspective view showing yet another stretchable clip of this invention.
FIG. 22 is a perspective view showing one method of placement of the stretchable clip shown in FIG. 21.
Figure 23:
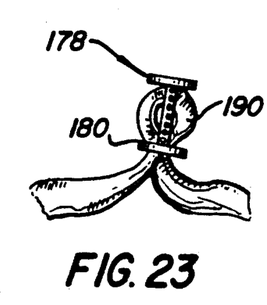
FIG. 23 is a perspective view showing another method of applying the stretchable clip illustrated in FIG. 21.

FIGS. 21-23 illustrates yet another stretchable ligature embodiment of this invention and two methods of placements of the ligature over and about an anatomical tubular structure. A clip 178 includes a pair of elastic memory bases 180, 182 which assume a quadrilateral configuration when forced open, as shown in FIG. 21. Bases 180, 182 are joined by a pair of legs 184, 186. The facing surfaces of legs may be provided with mating engaging structures. For example, pins 188 extend inwardly from leg 186 to be received in holes 189 in leg 184 and lock the legs together to enhance locking of the clip 178 onto the tissue being occluded. As shown in FIG. 22, a large loop 190 is formed in the tissue being occluded and the clip 178 is applied well below the upper end of the loop 190. In FIG. 23, the clip is applied over the loop 190 with only the base 180 performing the occluding function.

The term "ligature" as generally used in this application is intended to cover members such as rings, clips, plugs or caps for anatomical tubular structures within the scope of the present invention.

Figure 24:
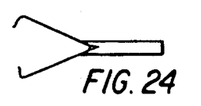
FIGS. 24 through 39 are side elevational views, with parts broken away, of different types of forceps mounted on the distal end of the inner tubular member of a surgical device of the present invention.
Figures 25, 26, 27, 29, 30, 31, 32, 33, 34, 35, 36, 37, 38, 39:
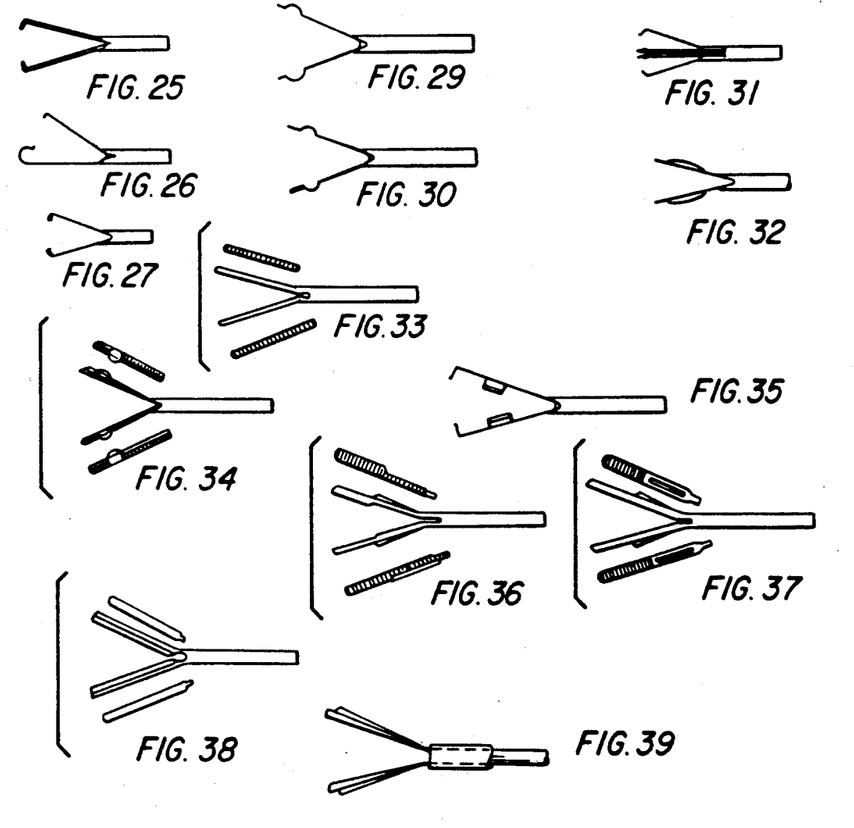
Figure 28:
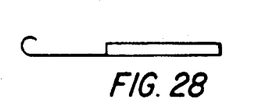

Different types of forceps for mounting on the distal ends of the interchangeable inner tubular members 12 are shown in FIGS. 24 through 39. In accordance with the principles of the present invention, these modified forceps are mounted on inner tubular members which can be readily interchanged with the tubular member 12 shown in FIG. 4, depending on the specific surgical application for the device 10 of the present invention. As illustrative examples, the forceps of FIG. 24 has overlapping end portions when they are closed and are suitable for use with occluding rings, while the forceps of FIGS. 25 and 27 have "kissing" or abutting end portions when closed and are suitable for use with stretchable clips. The forceps of FIG. 26 has a stationary hook-like member and a movable member while the forceps of FIG. 28 has a single hook-like member. The forceps of FIGS. 29 and 30 are provided with recessed or concave areas for holding a tubular structure or the like; the forceps of FIG. 31 has four members; the forceps of FIGS. 32 and 35 are provided with portions for cutting and holding a biopsy specimen; and the forceps of FIGS. 33, 34, 36, 37, 38 and 39 are provided with additional members to combine needle-holding cutting and biopsy functions along with clamping and scissor and knife cutting.

Figure 40:
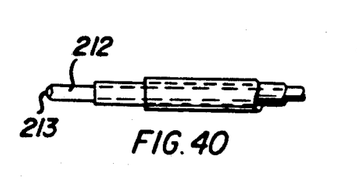
FIGS. 40 and 41 are side elevational views, with parts broken away, of end and side suction devices, respectively, on the distal end of the inner tubular member of the present invention.
Figure 41:
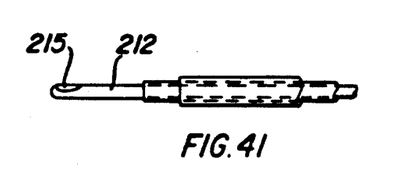

Referring to FIGS. 40 and 41, the distal end of the inner tubular member 212 may be open at its end portion 213 (FIG. 40) or at a side portion 215 (FIG. 41) for the purpose of applying suction to hold and move delicate tissue to produce a suction forceps function.

As shown in FIGS. 42 through 47, the surgical device 10 of the present invention may be utilized to insert a plug or the like in the utero-tubal junction in a reversible sterilization procedure.

Figures 42, 43, 44, 45, 46, 47:
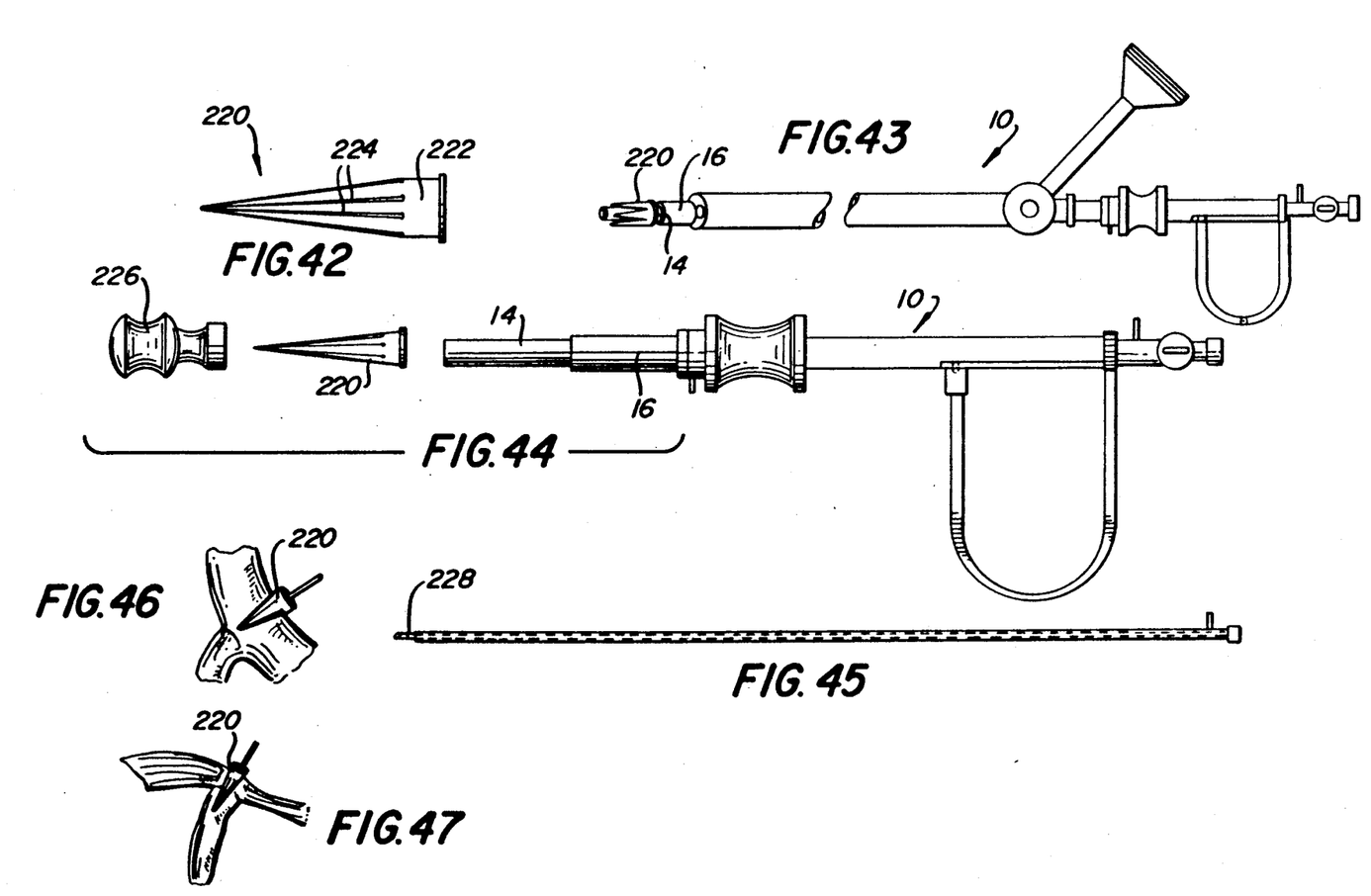
FIG. 42 is a side elevational view of a plug for the utero-tubal junction constructed in accordance with the principles of the present invention.
FIG. 43 is a side elevational view, with parts broken away, of a further embodiment of the surgical device of the present invention, with the utero-tubal junction plug removably mounted thereon.
FIG. 44 is an exploded side elevational view, showing the surgical device of FIG. 43, the plug of FIG. 42 and a pushing device for mounting the plug on the surgical device.
FIG. 45 is a side elevational view of a needle construction that can be used in conjunction with the surgical device shown in FIGS. 43 and 44.
FIGS. 46 and 47 are plan views, with parts broken away, showing a hysteroscopic plug and a laparoscopic plug, respectively, inserted in the utero-tubal junction.
Figure 48:
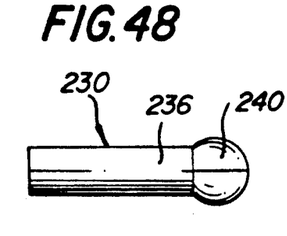
FIG. 48 is a side elevational view of a fimbrial cap constructed in accordance with the principles of the present invention.
Figure 49:
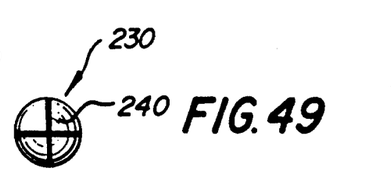
FIG. 49 is a front elevational view of the fimbrial cap shown in FIG. 48.

In a preferred embodiment, the plug 220 comprises a generally cylindrical base portion 222 and a plurality of flexible and resilient fingers 224 that are tapered to a pointed end portion and are normally closed, as shown in FIG. 42. In accordance with the operation of the surgical device 10 hereinbefore described, the plug 220 is mounted on the end portion of the middle tubular member 14 by being pushed thereon with a pusher device 226 of any desired construction. In this manner, the fingers 224 of the plug 220 are opened such that it is slidable over the middle tubular member 14 and is frictionally retained thereon, as shown in FIG. 43. Thereafter, the plug 220 may be inserted in the utero-tubal junction in a hysteroscopic procedure (FIG. 46) or a laparoscopic procedure (FIG. 47) by movement of the outer tubular member 16 into engagement with the base portion of the plug to push it off the middle tubular member 14 in a manner previously described herein. If desired, a needle 228 (FIG. 45) may be inserted through the middle tubular member 14 for the purpose of applying an anesthetic or the like during or before insertion of the plug 220 into the utero-tubal junction.

Referring to FIGS. 48 through 55, the surgical device 10 of the present invention can also be utilized to position a cap 230 over the fimbria 232 of the Fallopian tubes 234 in a reversible sterilization procedure. In a preferred embodiment, the cap 230 comprises an elongated, generally cylindrical body portion 236 with an elongated slit 238 therethrough so that the plug can be expanded for mounting on the end portion of the middle tubular member 14 in the manner shown in FIG. 50.

The cap 230 has an enlarged head portion 240 comprising a plurality of normally closed fingers 242 that are defined by transversed slots 244 in the head portion. The plug 230 is made of any suitable flexible and resilient material, such as a suitable plastic material so that the body portion 236 and head portion 240 thereof are normally closed in the manner shown in FIGS. 48, 49 and 51.

Figure 50:
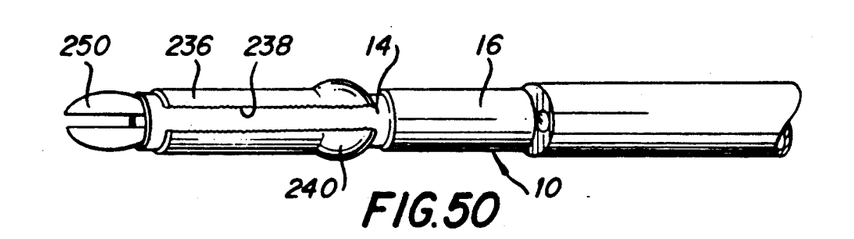
FIG. 50 is a side elevational view, with parts broken away, of another embodiment of the surgical device of the present invention, with the fimbrial cap removably mounted thereon.
Figures 51, 52, 53, 54:
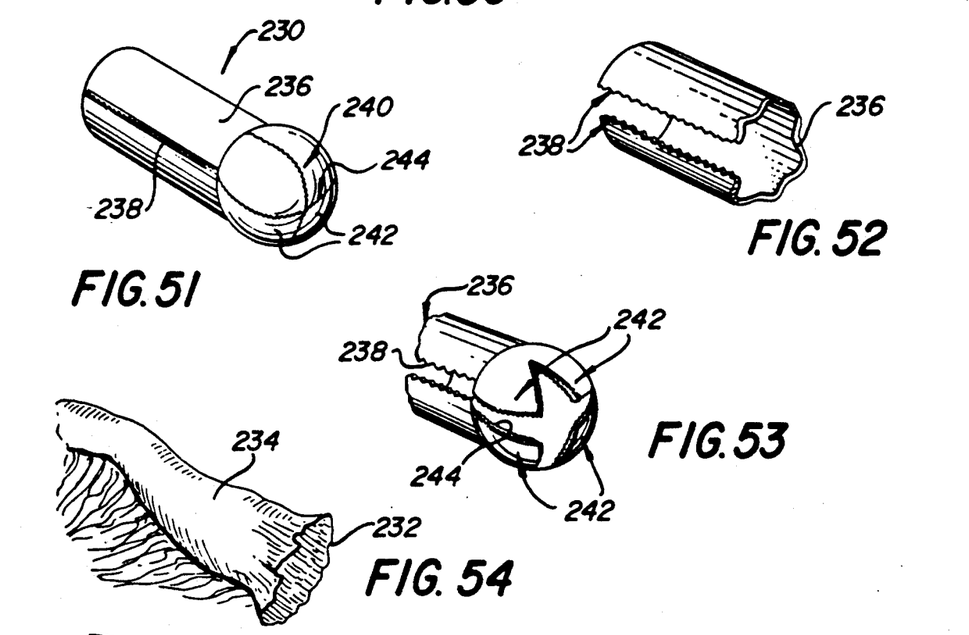
FIGS. 51, 52 and 53 are perspective views of the fimbrial cap, the rear portion thereof and the front portion thereof, respectively, shown in FIG. 48.
FIG. 54 is a perspective view of the fimbria at the entrance of the Fallopian tubes.
Figure 55:
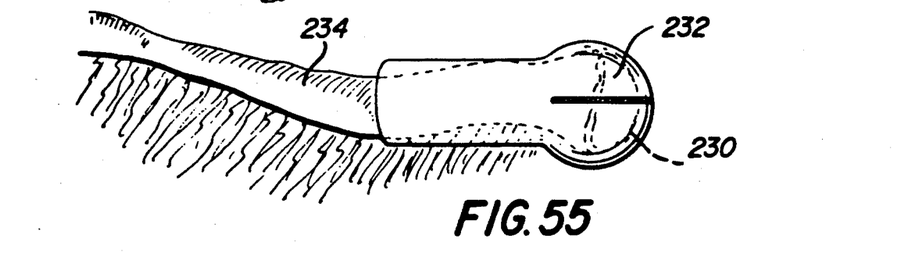
FIG. 55 is a perspective view showing the fimbrial cap positioned over the fimbria shown in FIG. 54.

In operation, the body portion 236 and head portion 250 of the plugs 230 are opened in any suitable manner to an extent such that the plug can be slidably and frictionally mounted on the distal end of the middle tubular member 14 of the surgical device 10 in the manner shown in FIG. 50. Through the use of suitable forceps 250 on the distal end of the inner tubular member 12, the tube 234 is grasped and then the plug 230 is positioned over the fimbria thereof, as shown in FIG. 55, by moving the outer cylinder 16 of the surgical device 10 into engagement with the head portion 240 of the plug 230 and pushing it off the middle tubular portion 14 in the manner previously described herein. It will be understood that the edges of the elongated slit 238 in the body portion 236 of the plug 230 may be serrated or otherwise constructed to increase the gripping power of the plug when it is positioned over the tube 234 by the surgical device 10.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come from within the meaning and range of equivalency of the claims are therefore intended to be embraced therein.

I claim:

1. A method of ligating and severing an anatomical tubular structure comprising the steps of
   applying a ligature to the anatomical tubular structure utilizing an applicator including a tubular member having a distal end carrying at least one ligature, an inner member movable within the tubular member and having a distal end carrying forceps means for engaging the anatomical tubular structure and positioning the anatomical tubular structure at the distal end of the tubular member and means for displacing the ligature from the distal end of the tubular member to engage and ligate the anatomical tubular structure;
   removing the inner member from the tubular member;
   inserting a cutting instrument through the tubular member, the cutting instrument having a distal end carrying means for cutting tissue; and
   cutting the anatomical tubular structure adjacent the ligature with the cutting means.

2. A method of ligating and severing an anatomical tubular structure as recited in claim 1 wherein said cutting step includes cutting a section of tissue from the anatomical tubular structure and further comprising the step of removing the section of the anatomical tubular structure from the body.

3. A method of ligating and severing an anatomical tubular structure as recited in claim 2 wherein the distal end of the cutting instrument includes means for capturing the section of anatomical tubular structure and said removing step includes withdrawing the cutting instrument through the tubular member.

4. A method of ligating and severing an anatomical tubular structure as recited in claim 1 wherein said ligature applying step includes ligating the anatomical tubular structure at spaced positions therealong and said cutting step includes cutting a section from the anatomical tubular structure between the spaced ligated positions.

5. A method of ligating and severing an anatomical tubular structure as recited in claim 4 wherein the cutting instrument distal end carries forceps members for cutting and capturing the section of the anatomical tubular structure and further comprising the step of removing the section of the anatomical tubular structure from the body by withdrawing the cutting instrument through the tubular member.

6. A method of plugging an anatomical tubular structure comprising the steps of inserting an applicator in the body including endoscope means, an elongate member having a distal end mounting a flexible, resilient plug in an expanded condition and means for displacing the plug from the distal end of the elongate member;

positioning the distal end of the elongate member adjacent the anatomical tubular structure using the endoscope means for viewing; and positioning the plug within the anatomical tubular structure by displacing the plug from the distal end of the elongate member.

* * * * *